United States Patent
Parker

(10) Patent No.: US 10,352,887 B1
(45) Date of Patent: Jul. 16, 2019

(54) CONDUCTIVITY MEASUREMENT METHODS AND SYSTESMS

(71) Applicant: Ronald W. Parker, Clinton, CT (US)

(72) Inventor: Ronald W. Parker, Clinton, CT (US)

(*) Notice: Subject to any disclaimer, the term of this patent is extended or adjusted under 35 U.S.C. 154(b) by 0 days.

(21) Appl. No.: 15/619,653

(22) Filed: Jun. 12, 2017

Related U.S. Application Data

(60) Provisional application No. 62/353,180, filed on Jun. 22, 2016.

(51) Int. Cl.
 *G01N 27/02* (2006.01)
 *G01N 27/06* (2006.01)

(52) U.S. Cl.
 CPC ........... *G01N 27/06* (2013.01); *G01N 27/028* (2013.01)

(58) Field of Classification Search
 CPC ........ G01N 27/06; G01N 27/45; G01N 27/07; G01R 27/08
 USPC ......................................... 324/443, 654, 649
 See application file for complete search history.

(56) References Cited

U.S. PATENT DOCUMENTS

| | | | | |
|---|---|---|---|---|
| 4,656,427 A * | 4/1987 | Dauphinee | ............. | G01N 27/07 204/400 |
| 6,781,389 B1 * | 8/2004 | Colvin | ................... | G01N 27/07 324/449 |
| 8,525,533 B2 | 9/2013 | Sullivan | | |
| 8,975,901 B2 | 3/2015 | Birecki et al. | | |
| 8,981,795 B2 | 3/2015 | Jagiella et al. | | |
| 9,086,357 B2 | 7/2015 | Howell et al. | | |
| 9,310,237 B2 | 4/2016 | Roper et al. | | |
| 9,329,296 B2 | 5/2016 | Jung et al. | | |
| 9,354,193 B2 | 5/2016 | Platte et al. | | |
| 2009/0125250 A1 * | 5/2009 | Wang | ..................... | G01N 27/06 702/30 |
| 2011/0316564 A1 * | 12/2011 | Park | ....................... | G01N 27/06 324/672 |

(Continued)

OTHER PUBLICATIONS

Rajendran, A. and Neelamegam, P. "Design and development of microcontroller based conductivity measurement system", Indian Journal of Pure & Applied Physics, Mar. 2004, pp. 182-188,vol. 42, IPC Code: G01H 25/20.

*Primary Examiner* — Albert K Wong

(57) ABSTRACT

A method for accurately measuring the electrical conductivity of substances. This method incorporates two points of measurement that are isolated from each other. Each of these points is in contact with the substance to be measured. A continuous, constant electrical current is passed through the substance at the measurement points by means of an electrical force that is not constant but varies depending upon the amount of electrical force required to maintain the constant electrical current through the substance. This constant current is passed through the substance in two directions. This change in direction is achieved by reversing the polarity of the electrical force across the two measurement points. The time periods for each of the two directions of constant current flow are equal. The amount of electrical force or voltage that is required to maintain this constant amount of current is directly related to the resistance of the substance. This electrical force that represents the resistance of the substance can then be converted into a second electrical force that represents the conductivity of the substance by means of a divider circuit.

8 Claims, 9 Drawing Sheets

(56) References Cited

U.S. PATENT DOCUMENTS

| | | | | |
|---|---|---|---|---|
| 2013/0234706 A1* | 9/2013 | Mandal | ................ | G01N 24/081 |
| | | | | 324/303 |
| 2014/0015551 A1* | 1/2014 | Russ | ..................... | G01N 27/06 |
| | | | | 324/693 |
| 2015/0260671 A1* | 9/2015 | Press | ................... | G01N 27/045 |
| | | | | 324/706 |

* cited by examiner

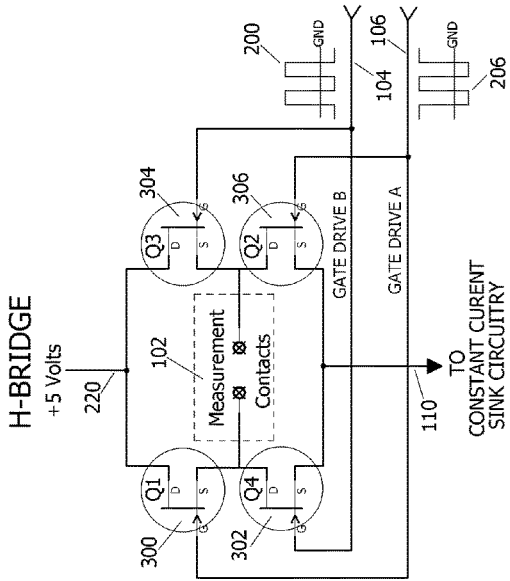
Fig. 3
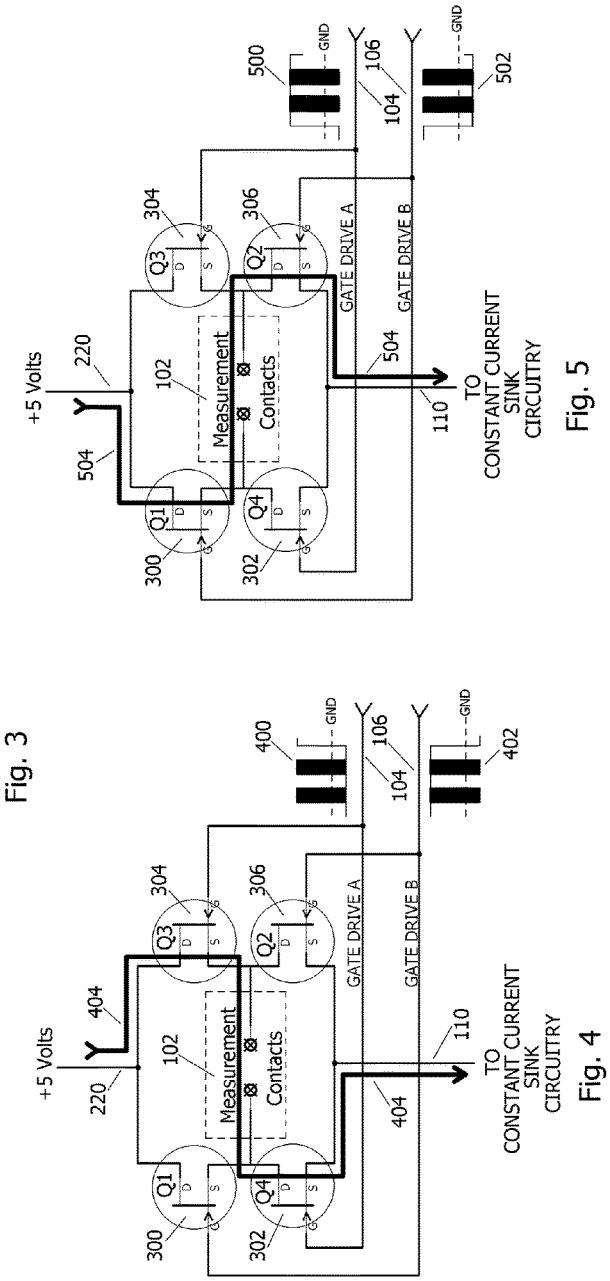
Fig. 5
Fig. 4

CONDUCTIVITY MEASUREMENT METHODS AND SYSTESMS

CROSS-REFERENCE TO RELATED APPLICATION

This application claims priority under 35 U.S.C. § 119 to U.S. Provisional Patent Application No. 62/353,180, filed Jun. 22, 2016, the contents of which are incorporated herein by reference in their entirety.

BACKGROUND

1. Field

This invention relates generally to a method of measuring conductivity, and more particularly to a method of measuring the resistance and conductivity of substances that contain polar molecules or polar compounds, ionic molecules or ionic compounds, or free radicals such as those found in acids and bases.

2. Description of Related Art

The consistent measurement of conductance in ionic and polar substances, usually in a liquid or fluid state, is not as straightforward as the measurement of conductance of an electrical resistor. The reason for this lies in the nature of the substance being measured. When an electrical potential is applied across a polar substance or a substance containing ions, the value of the conductance is inconsistent and will change with time. Normally, this inconsistency resembles the charging or discharging of a capacitance. This conductance change is due to an alignment of the ions or polar molecules of the substance between the points at which the electrical potential is being applied. This alignment is in response to the magnitude and polarity of the applied electrical potential and cause the conductance of the substance to be affected.

Some methods for measuring conductivity use a constant electrical force that is applied across contact points that are in intimate contact with the substance whose conductivity is to be measured. To minimize galvanic action, the polarity of this constant electrical force is reversed at repeated intervals. However, any capacitance or inductance across the contact points will affect the constant electrical force and will result in inaccurate conductivity measurements. In some applications that use these methods, a calculation of the rate of change of measurement is used to predict a measurement value. Since this is not a direct measurement, the calculation itself can introduce measurement error.

Still other methods of conductance measurement use one or more electric fields that are generated by inductive components. These fields are used to measure the effects that the substance being measured has on these fields. This too is not a direct measurement and can result in measurement errors.

There remains a need for a method that can accurately and efficiently measure the resistance and conductivity of substances, especially substances which contain polar, ionic, or free-radical components.

SUMMARY

Accordingly, it is an object of the invention to provide a method for accurately measuring the conductivity of substances. In one exemplary embodiment, this is accomplished by passing a constant value of current, by means of electrical contact points, through a substance to be measured and continuously measuring the amount of electrical force, or voltage, needed to maintain this constant current. In one exemplary embodiment, the polarity of the electrical force used to generate the constant current may be continuously reversed.

This prevents the polar, ionic, and free-radical components from gathering about the measurement points, a situation that can affect the accuracy of the measurements. In addition, erosion and/or product build-up on the measurement points is minimized by reversing this constant current. Continuously reversing the electrical force used to generate the constant current may also serve to minimize the physical alignment of polar, ionic, and free-radical components of the substance located between the measurement points. The electrical force, or voltage needed to produce the constant current is directly related to the resistance value of the substance. By dividing the resistance value into '1', the inverse of the resistance value, which is the conductivity value, will be obtained.

There are three additional factors that can affect the accuracy of conductivity measurements. The first factor is the area of the conductive material connected to the measurement points or, in cases where the only points in contact with the substance are the actual measurement points, the area of the measurement points themselves. These areas have known tables of values that are used to produce accurate measurements of conductivity. The second factor is the type of conductive material used. Conductive materials also have known tables of values that are used to produce accurate measurements of conductivity. The third factor is the temperature of the substance being measured. These temperatures also have known tables of values that are used to produce accurate measurements of conductivity. Temperature compensation can be included in the measurement circuitry, or it can be added to the final measurement of conductivity as an offset.

There is provided a method for accurately measuring the conductivity of a substance. In one exemplary embodiment, this method incorporates two points of measurement that are isolated from each other. Each of these points is in intimate contact with the substance to be measured. A continuous, constant electrical current is passed through the substance being measured at the measurement points by means of an electrical force that is not constant but varies depending upon the amount of electrical force required to maintain the constant electrical current through the substance being measured. This constant current is passed through the substance in two directions. This change in direction is achieved by reversing the polarity of the electrical force across the two measurement points. The periods of time for each of the two directions of constant current flow are equal. The amount of electrical force or voltage that is required to maintain this constant amount of current is directly related to the resistance of the substance being measured. Since resistance is the inverse of conductance, when a value of '1' is divided by the resistance value of the substance being measured, the result is the conductivity of the substance being measured.

A system for measuring conductance of a substance is disclosed, including: a plurality of electronic circuits; two or more contact points coupled to the plurality of electronic circuits, each of the contact points being in conductive contact with a substance; wherein the electronic circuits are configured to apply a constant current of alternating direction to the contact points such that the constant current passes through the substance; wherein the electronic circuits are further configured to produce an output voltage when the constant current of alternating direction is applied to the substance, wherein the output voltage corresponds to the conductivity of the substance.

BRIEF DESCRIPTION OF THE DRAWINGS

FIG. 3 is a circuit diagram illustrating the H-bridge in one exemplary embodiment of the invention;

FIG. 4 illustrates the path taken by the current through a substance being measured when a first direction of current through the H-Bridge shown in FIG. 3 has been selected;

FIG. 5 illustrates the path taken by the current through a substance being measured when a second direction of current through the H-Bridge shown in FIG. 3 has been selected;

DETAILED DESCRIPTION

Figure 1:
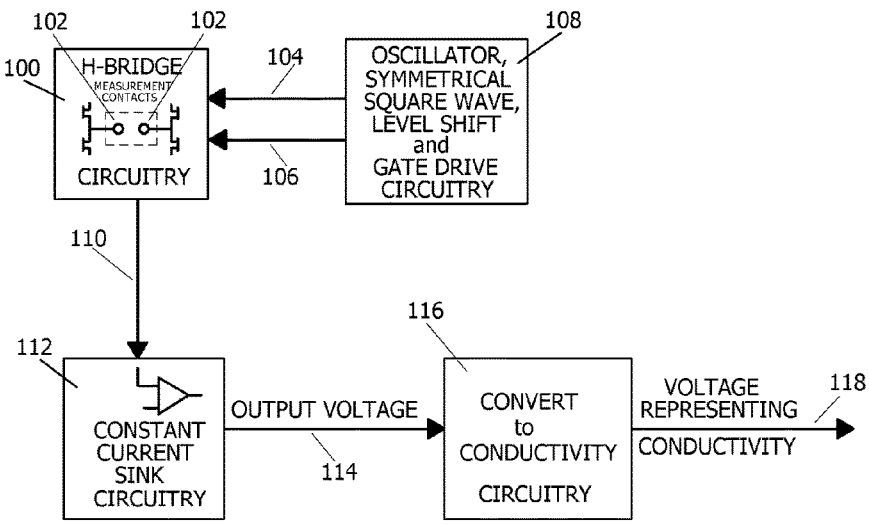
FIG. 1 is a block diagram illustrating the core circuitry in one exemplary embodiment of the invention, including the H-bridge circuitry, the constant current sink circuitry, and the convert to conductivity circuitry.

The following detailed description refers to the accompanying drawings, however the detailed description and the accompanying drawings do not limit the invention; the scope of the invention is defined by the appended claims.

The apparatuses, methods, and systems (herein after the Measurement System) for measuring conductivity described in this specification may be used for measuring the electrical conductivity of liquid, solid, and gaseous substances. The Measurement System may be configured to accurately and consistently make linear measurements of the relative conductivity of fluids that contain polar substances (water, for example), ionic substances such as acids and bases, and substances that contain free radicals. In one embodiment, the Measurement System is an electronic system that uses an electrical current to measure conductivity of substances. The electrical current may be applied in a specific way to obtain accurate and consistent linear measurements of conductivity.

In one exemplary embodiment, the Measurement System incorporates two points of electrical measurement, each of which can be connected to one or more areas of conductive material in contact with a substance being measured. In the absence of these areas of conductive material, each of the two points of electrical measurement can themselves be in contact with the substance being measured. In these exemplary embodiments, there is no physical contact between the two measurement points themselves or between the areas of conductive material to which each of the measurement points are connected.

Using the conductive material or measurement points as current paths, a continuous, constant amount of electrical current may be passed through the substance being measured. An electrical force, or voltage, may be used to maintain the flow of constant current. This electrical force responds rapidly to load changes such as current changes caused by the charging or discharging of load inductances or capacitances. The result is a stable and accurate measurement of the resistance of the substance. The amount of electrical force or voltage that is required to maintain this constant amount of current is directly related to the resistance of the substance. The conductance of the substance is simply the inverse of the resistance:

$$\text{Conductance} = \frac{1}{\text{Resistance}}$$

In one exemplary embodiment, the constant electrical current may be passed through the substance in two directions by rapidly reversing the polarity of the electrical force applied to the measurement points. The time periods for each of the two directions of constant current flow are equal. Therefore, the frequency of these reversals is constant. The period of time between these polarity reversals is measured in the range of millisecond to tens of milliseconds. By contrast, the time required to reverse the direction of current is measured in nanoseconds.

When an electrical force, or voltage, is applied across a substance, the polar, ionic and free-radical components of the substance tend to migrate toward the measurement points. The direction of this migration depends upon the polarity of the polar, ionic or free-radical components of the substance being measured. These components of the substance will collect about the measurement points and will resist the flow of current between the measurement points. The result is an apparent change in the conductivity of the substance. This apparent change normally mimics the charging of a capacitance through some value of resistance. When resistance or conductivity measurements are made, this apparent change can produce errors in the results.

By continually reversing the direction of the constant current, the polar, ionic or free-radical components of the substance being measured are not allowed to migrate or to become aligned with each other. In addition, galvanic action which could erode, corrode, or otherwise physically alter the measurement points, is minimized. The result of this reversal of electrical current is to provide more stable and consistent measurements of conductivity.

FIG. 1 is a block diagram showing one exemplary embodiment of the electronic circuitry used by the Measurement System. The output of this circuitry 118 may be a voltage that is directly related to the conductivity of the substance being measured. The Constant Current Sink Circuitry 112 produces the continuous current used by the Measurement System. This current will travel from one Measurement Contact 102 to the other Measurement Contact 102 by passing through the substance being measured. The H-Bridge 100 may be used to reverse the direction of the constant current through the substance being measured. Reversing the direction of current is also a feature of the method that may be used by the Measurement System. The period of time between these reversals of current may be determined by the Oscillator and Symmetrical Square Wave components of the Oscillator, Symmetrical Square Wave, Level Shift and Gate Drive Circuitry 108. In one exemplary embodiment, the gate drive signals 104,106 for the H-Bridge 100 may be generated by the Level Shift and Gate Drive components of the Oscillator, Symmetrical Square Wave, Level Shift and Gate Drive Circuitry 108. In this exemplary embodiment, the Output Voltage 114 from the Constant Current Sink Circuitry 112 directly reflects the resistance of the substance being measured, where the substance being measured is located between the Measurement Contacts 102. As shown in FIG. 1, the Output Voltage 114 may be connected to the input of the Convert to Conductivity Circuitry 116.

Conductivity is the inverse of resistance. In mathematical terms, conductivity is equal to 1 divided by resistance. In one exemplary embodiment of the Measurement System, the Convert to Conductivity Circuitry 116 can perform the divide operation that is necessary to convert units of resistance into units of conductivity. The output of the Convert to Conductivity Circuitry 116 is the Voltage Representing Conductivity 118. This voltage represents the conductivity, in units of Siemens (S) or microsiemens (μS), of the substance being measured.

Figure 2:
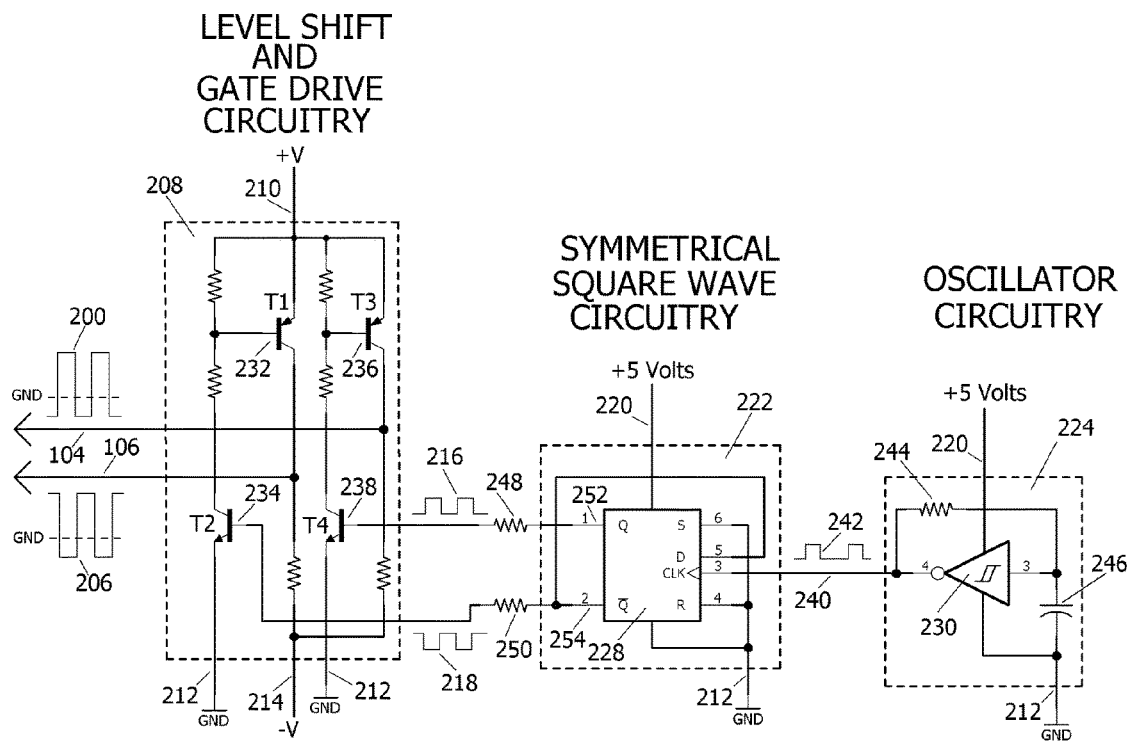
FIG. 2 is a circuit diagram showing one of many possible circuits that can be used to produce the reversal of current at equal periods of time through a substance being measured, in accordance with one exemplary embodiment of the invention.

FIG. 2 is a schematic of one exemplary embodiment of circuitry that can be used by the Measurement System to generate the signals necessary to drive the transistors of the H-Bridge 100 shown in FIG. 1. The Oscillator Circuit 224 may include a Schmitt Trigger Input Inverter 230, a resistor 244, and a capacitor 246. The resistor 244 and capacitor 246 may form a timing network that is in a feedback loop around the Inverter 230. The output of the Inverter 240 may be a continuous, asymmetrical wave 242 that oscillates at a frequency determined by the values of resistor 244 and capacitor 246.

Because of the asymmetry of this output, in one exemplary embodiment, the signal 242 is sent to the input of the Symmetrical Square Wave Circuitry 222. This circuit may contain a D-Latch 228 that is in a "Divide by 2" configuration. The rising edge of the signal 242 out of the Inverter 240 causes the 'Q' 252 and 'Q-Not' 254 outputs of the D-latch 228 to change state, which results in output signals 216, 218 from the D-Latch 228, that are equal in period for both their high and low output states. In other words, these are symmetrical square wave output signals.

In one exemplary embodiment, of the Measurement System, the 'Q' 252 and 'Q-Not' 254 outputs of the D-Latch 228 are opposite in polarity, so that each output drives one half of the Level Shift and Gate Drive Circuitry 208. In one exemplary embodiment, the +V power supply 210, the −V power supply 214 and the +5 Volts 220 power supply are all filtered D.C. (Direct Current) power supplies with a common return path at GND 212 (ground). In this case, the output voltages from the +V 210 power supply and the −V 214 power supplies are more than sufficient to fully turn on and fully turn off the H-Bridge 100 transistors, Q1 300, Q2 306, Q3 304 and Q4 302. At the outputs of the D-Latch 228 are resistors 248, 250 that can be used to limit the base current to T4 238 and T2 234 of the Level Shift Circuitry 208. The Level Shift and Gate Drive Circuitry 208 may be used to increase the positive and negative voltage levels of both of the D-Latch 228 output signals 252, 254. The resulting signals 104, 106 appear at the output of the Level Shift and Gate Drive Circuitry 208. The waveforms 200, 206 that represent the increased voltage signals are shown as they relate to power supply common, or GND 212 (ground).

FIG. 3 is a schematic of an exemplary embodiment of the H-Bridge 100 shown in FIG. 1. This exemplary H-Bridge configuration satisfies that part of the method used by the Measurement System that deals with reversing the current through the measurement points that are indicated in FIG. 1 and FIG. 3 and in subsequent figures as the Measurement Contacts 102. The H-Bridge configuration allows current to flow through the Measurement Contacts 102 in both directions. In the embodiment shown, the transistors that are labeled Q1 300, Q2 306, Q3 304 and Q4 302 are J-FET transistors, all of which have the same specifications. These transistors have an extremely low 'On' resistance and an extremely high 'Off' resistance. Electrical current leakage between elements of these transistors is also extremely low.

In the schematic shown in FIG. 3, the path for current begins at +5 Volts 220. This is a 5 Volt filtered D.C. (Direct Current) power supply. When the transistors Q1 300, Q2 306, Q3 304 and Q4 302 are properly sequenced On and Off, current passes through the measurement contacts 102 and then continues on to the Constant Current Sink circuitry 112 through the wire connection 110 between the H-Bridge 100 circuitry and the Constant Current Sink circuitry 112.

FIG. 4 illustrates the path taken by the current through a substance being measured when a first direction of current through the H-Bridge 100 has been selected in one exemplary embodiment of the Measurement System. As shown in FIG. 4, the darkened areas of the GATE DRIVE A 104 waveform 400, that is used to drive the gates of transistors Q3 304 and Q4 302, indicates that sufficiently high voltage levels have been applied so as to force these transistors to fully conduct. At the same time, the darkened areas of the GATE DRIVE B 106 waveform 402, that is used to drive the gates of transistors Q1 300 and Q2 306, indicates that sufficiently low voltage levels have been applied so as to force these transistors not to conduct. The direction of the current path through the measurement contacts 102 is shown in FIG. 4 by the darkened arrow 404. This arrow 404 indicates that the current path passes through the Measurement Contacts 102 in a right-to-left direction and then passes downward to the Constant Current Sink Circuitry 112 of FIG. 1.

FIG. 5 illustrates the path taken by the current through a substance being measured when a second direction of current through the H-Bridge 100 has been selected in the exemplary embodiment of the Measurement System. As shown in FIG. 5, the darkened areas of the GATE DRIVE B 106 waveform 502, that is used to drive the gates of transistors Q1 300 and Q2 306, indicates that sufficiently high voltage levels have been applied so as to force these transistors to fully conduct. At the same time, the darkened areas of the GATE DRIVE A 104 waveform 500 that is used to drive the gates of transistors Q3 304 and Q4 302 indicates that sufficiently low voltage levels have been applied so as to force these transistors not to conduct. The direction of the current path through the measurement contacts 102 is shown in FIG. 5 by the darkened arrow 504. This arrow 504 indicates that the current path passes through the Measurement Contacts 102 in a left-to-right direction and then passes downward to the Constant Current Sink Circuitry 112 of FIG. 1.

In one exemplary embodiment of the Measurement System, the circuitry shown in FIG. 2 may be used to produce Gate Drive A 104 and Gate Drive B 106 signals. In one embodiment, both of these signals are symmetrical square waves, but are of opposite polarities. This circuitry may be configured to produce the two current paths described above in the schematics of FIG. 4 and FIG. 5, so that the part of the proposed method used by the Measurement System that deals with reversing current through the measurement contacts 102 while maintaining equal periods of time between reversals will be satisfied.

Figure 6:
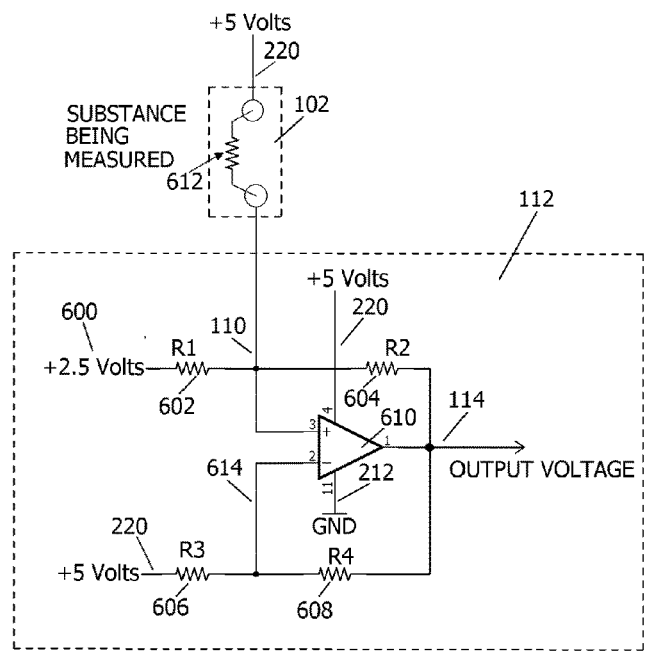
FIG. 6 is a circuit diagram showing an exemplary constant current sink circuitry connected to a substance being measured, in one exemplary embodiment of the invention.

FIG. 6 is an exemplary schematic representation of the circuitry referenced in FIG. 1 as the Constant Current Sink Circuitry 112. The explanation of the operation of the H-Bridge 100 circuitry of FIG. 3, FIG. 4, and FIG. 5 shows that the circuit operation results in a continuous current path through the H-Bridge 100 circuitry and that the current, at circuit location 110, flows in only one direction. For that reason, and to simplify the explanation of the operation of the Constant Current Sink Circuitry 112, a representation of the H-Bridge 100 circuitry consisting solely of the Measurement Contacts 102 and a Substance Being Measured 612 are shown in FIG. 6.

In one exemplary embodiment of the Measurement System, the Constant Current Sink Circuitry 112 shown in FIG. 6 may be powered by regulated and filtered +5 Volts 220 and +2.5 Volts 600 D.C. (Direct Current) power supplies. The return current path for these power supplies may be through GND 212 (ground). In FIG. 6, the operational amplifier 610 is the active component of the circuit. This amplifier may be a rail-to-rail device, meaning that the output voltage 114 of the operational amplifier 610 can traverse nearly the full range of the device's +5 Volts 220 power supply voltage, minus a few millivolts (mV).

In one exemplary embodiment, the '+' 110 and '−' 614 inputs to the operational amplifier 610 have extremely high input impedances, resulting in input currents that are less than 150 femtoamperes (fA), one femtoampere being $10^{-15}$ Amperes. In one embodiment, all four resistors, R1 602, R2 604, R3 606 and R4 608, of this circuit have the same value. As an example of the operation of the Constant Current Sink Circuit 112, let the value of each of the four resistors, R1 602, R2 604, R3 606, and R4 608 be 500 kiloohms (kΩ). The value of the constant current being sunk can be determined by calculating the current through the Substance Being Measured 612 when the Substance Being Measured 612 has a value of zero ohms. This places +5 Volts 220 at the '+' 110 input of the operational amplifier. In this configuration, the '+' 110 and '−' 614 inputs of the operational amplifier 610 are always attempting to be equal in voltage. The '−' 614 input of the operational amplifier must therefore be +5 Volts. This now places +5 Volts on both ends of resistor R3 606 and no current will flow through R3 606. Consequently, there is effectively no current through R4 608 because there is negligible current used by the very high impedance of the '−' 614 input of the Operational Amplifier 610. As a result, both ends of R4 608 must be at a +5 Volt potential. In order for this to occur, the Output Voltage 114 of the operational amplifier 610 must also be at a potential of +5 Volts. There remains only one path for the current through the Substance Being Measured 612. That path is through R1 602 to the 2.5 Volts 600 power supply. This current will have a value of:

$$\frac{+5\text{ V} - 2.5\text{ V}}{500\text{ k}\Omega} \text{ or } 5\text{ μA}$$

In this example, five microamps is the value of the current this circuit will produce for all values of the Substance Being Measured 612, when the value of the Substance Being Measured 612 falls between 500 kΩ and zero ohms.

As another example, let the value of the Substance Being Measured 612 be 500 kΩ With a constant current of 5 μA, the voltage that is dropped across the Substance Being Measured 612 will be:

$$5\text{ μA}*500\text{ k}\Omega \text{ or } 2.5\text{V}$$

In one exemplary embodiment, the top end of the Substance Being Measured 612 is at a potential of +5 Volts 220. Subtracting 2.5 Volts from this value leaves 2.5 Volts at the bottom end 110 of the Substance Being Measured 612, which is also the junction of R1 602, R2 604 and the '+' 110 input of the operational amplifier. With the 2.5 Volts 600 source at one end of R1 602 and 2.5 Volts at the other, or junction end of R1 602, there will be no current through R1 602. With 2.5 Volts at the '+' 110 input to the operational amplifier 610, the '−' 614 input of the operational amplifier 610 must also be at 2.5 Volts. This places 2.5 Volts across R3 606, which produces a current through R3 606 of:

$$\frac{2.5\text{ V}}{500\text{ k}\Omega} \text{ or } 5\text{ μA}$$

The direction of this current through R3 606 is from the end of R3 606 that is connected to +5 Volts 220, to the end of R3 606 that is the junction of R3 606 and R4 608. This same current will flow through resistor R4 608, producing a Voltage drop across R4 608 of:

$$5\text{ μA}*500\text{ k}\Omega \text{ or } 2.5\text{V}$$

The direction of the 5 micro-Amp current through R4 608 will be from the junction of R3 606 and R4 608 toward the Output 114 of the operational amplifier 610. With 2.5 Volts at the junction of R3 606 and R4 608, the Output Voltage 114 of the operational amplifier 610 must be zero Volts in order to sink the 5 micro-Amps of current that pass through R4 608. With zero Volts at the output 114 of the operational amplifier 610 the voltage across R2 604 will now be 2.5 Volts. The current through R2 604 must then be:

$$\frac{2.5\text{ V}}{500\text{ k}\Omega} \text{ or } 5\text{ }\mu\text{A}$$

The output 114 of the operational amplifier 610 will sink this 5 microamps of current.

Figure 8:
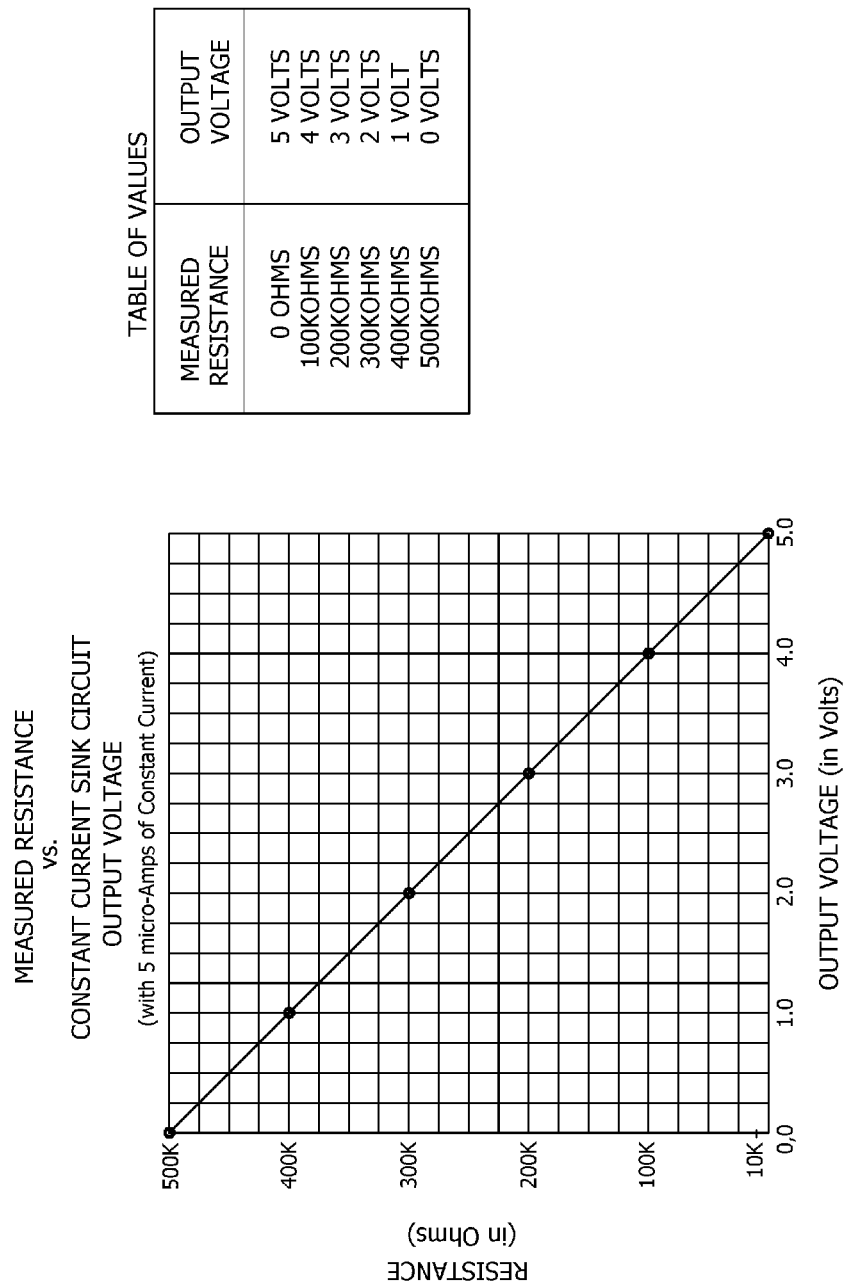
FIG. 8 is a graph showing resistance of a substance being measured as it relates to the output voltage of a constant current sink circuit in one exemplary embodiment of the invention.

In reference to the table of values shown in FIG. 8, the Output Voltage 114 of the operational amplifier has been calculated for several values of the resistance for the Substance Being Measured 612 in order to verify the linearity of the relationship between Output Voltage 114 and the resistance of the Substance Being Measured 612. These values have been plotted on the graph shown in FIG. 8.

The maximum resistance that can be measured by the Constant Current Sink Circuitry 112 is equal to the resistance value of one of the equally valued resistors, R1 602, R2 604, R3 606 or R4 608, shown in FIG. 6. In the exemplary embodiment shown in FIG. 6, a value of 500 kΩ for each of these four resistors was assumed. This was the value of the maximum resistance of the Substance Being Measured 612 that could be measured across the Measurement Contacts 102. This relationship is true for all of the resistance values that these four equally valued resistors can take. The full output range of 0 Volts to +5 Volts will remain the same no matter what value of resistance is used, however, the amount of constant current that is being sunk will increase with lower resistance values and decreased with higher resistance values. For lower resistance values, the maximum output current capability of the Operational Amplifier 610 will be the limiting factor.

Figure 7:
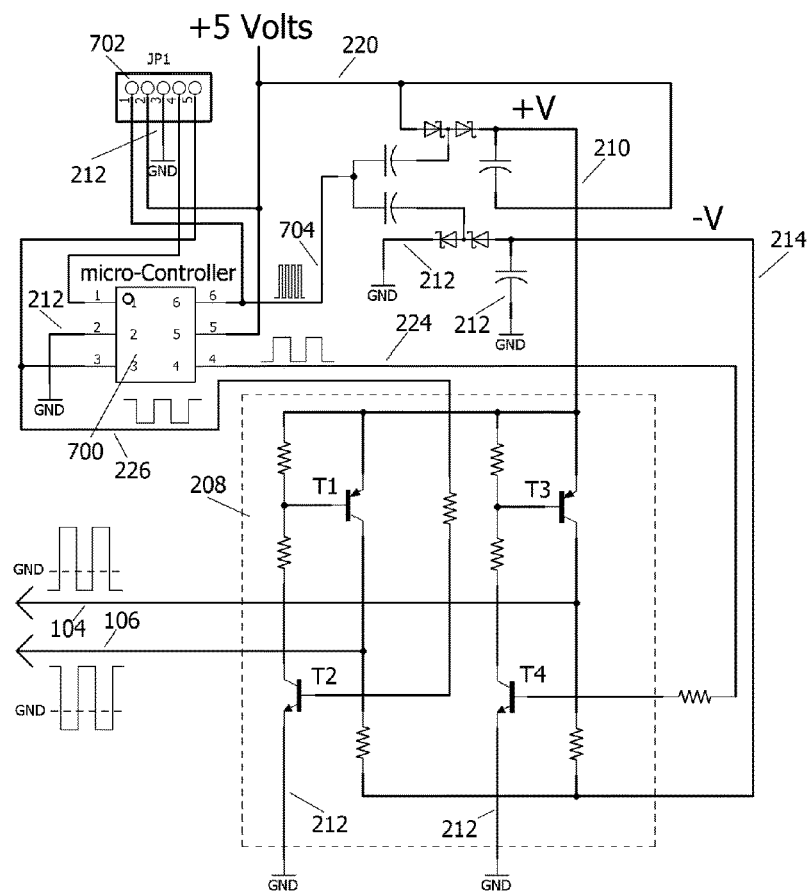
FIG. 7 is a circuit diagram showing an example of a circuit that can be used in one exemplary embodiment of the invention to produce the reversal of current at equal periods of time through a substance being measured by using a micro-controller.

FIG. 7 is a schematic of a circuit that will generate the same pulse signals as those generated by the Oscillator Circuitry 224 of FIG. 2 and the Symmetrical Square Wave Circuitry 222 of FIG. 2. In one exemplary embodiment, the +5 Volts 220 power supply for this circuitry is a regulated, filtered D. C. Voltage source, and the return path for this +5 Volts 220 power supply is GND (ground) 212. The circuit shown in FIG. 7 may utilize a microcontroller 700 that generates signals 224, 226 used to drive the Level Shift and Gate Drive Circuitry 208. The Level Shift and Gate Drive Circuitry 208 may be used to generate the H-Bridge transistor gate drive signals 104, 106. The micro-Controller 700 may also provide a signal 704 that can be used to drive voltage doubling and negative signal generating circuitry that can provide both the +V 210 and the −V 214 voltages used by the Level Shift and Gate Drive Circuitry 208. In one exemplary embodiment, the microcontroller 700 can be programmed by means of an external jack 702.

Figure 9:
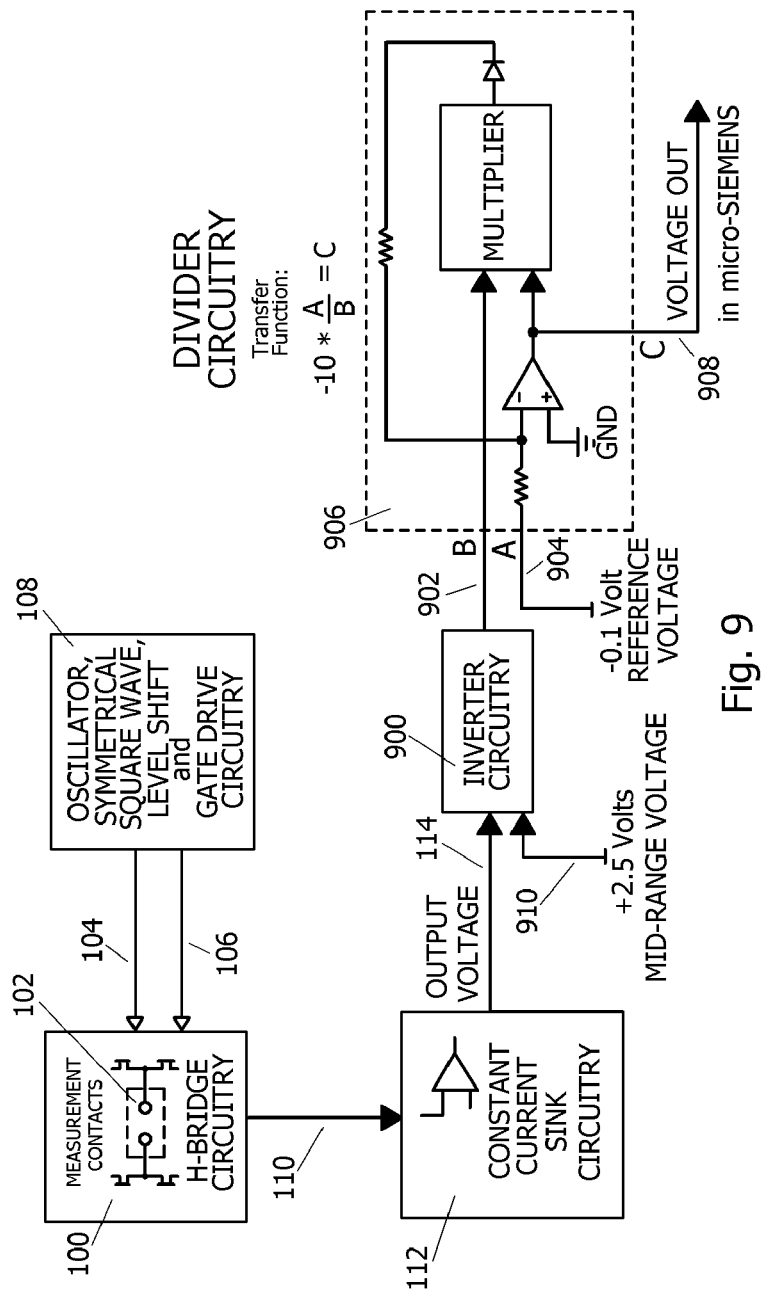
FIG. 9 is a block diagram of a system of conductivity measurement according to one exemplary embodiment of the invention.

FIG. 9 is a block diagram of another exemplary embodiment of the Measurement System. In addition to the previously discussed components found in FIG. 1 100, 108, 112, this embodiment includes Inverter Circuitry 900 and Divider Circuitry 906. The Divider Circuitry 906 shown in the embodiment incorporates a multiplier circuit that has been configured as a divider circuit. The Output Voltage 114 from the Constant Current Sink Circuitry 112 must be inverted about the Mid-Range Voltage 910, which is +2.5 Volts, in order to achieve the correct output from the Divider Circuitry 906. This inversion produces a signal 902 that ranges from zero Volts to +5 Volts as the resistance of the substance being measured varies from zero ohms to 500 kΩ. This relationship can be seen in the graph of FIG. 11A entitled, "Measured Resistance vs. Inverter Circuit Voltage Out". This graph is the inverse of the graph of FIG. 8. The voltage out 902 from the Inverter 900 of FIG. 9 forms the B 902 input to the Divider 906. The transfer function of the Divider is:

$$-10 * \frac{A}{B} = C$$

The A 904 input to the Divider 906 is a voltage with a value of −0.1 Volts. Since the B 902 input voltage is a positive voltage, the result of multiplying this negative A 904 input voltage by the '−10' term in the above formula, will produce a positive C 908 value. The result is a positive Voltage Out 908 that represents microsiemens (µS) of Conductivity.

Figure 10:
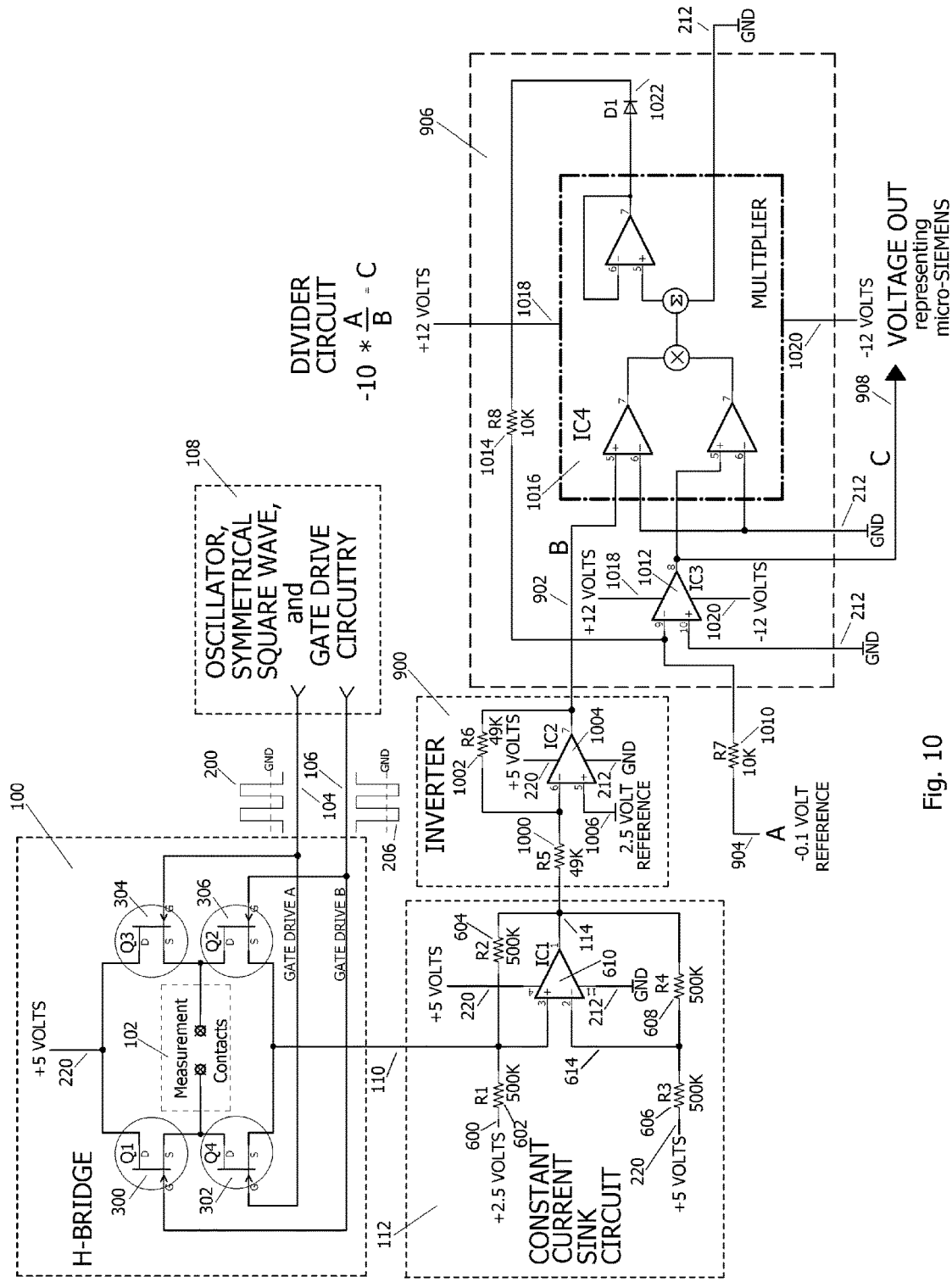
FIG. 10 is a schematic of a system of conductivity measurement that includes an inverter circuit and a divider circuit that may be used to produce a voltage representation of the conductivity of a substance being measured, in accordance with one exemplary embodiment of the invention.

FIG. 10 shows circuitry that is based upon the block diagram of FIG. 9. As with previous descriptions, the H-Bridge 100 and Constant Current 112 circuits are used to convert the resistance value of the substance being measured, that is across the Measurement Contacts 102, into an Output Voltage 114 that linearly represents this resistance. The details of the Oscillator, Symmetrical Square Wave, and Gate Drive Circuitry 108 are not included in this schematic. Circuitry for both the Inverter 900 and the Divider Circuit 906 has been included in FIG. 10.

Figure 11A:
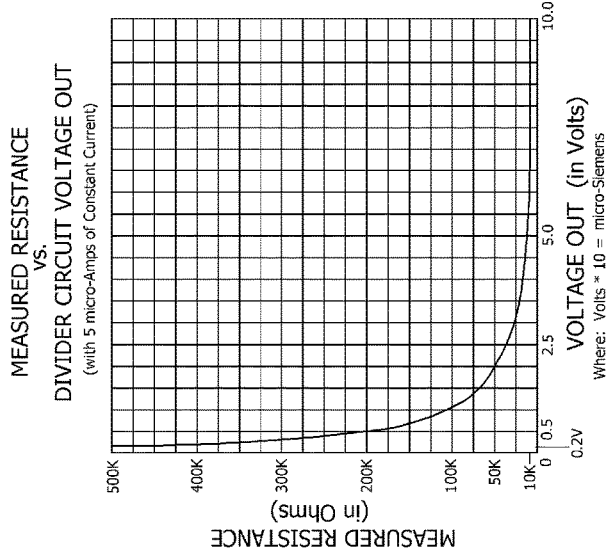
FIG. 11A is a graph showing the resistance of a substance being measured versus the output voltage of the inverter circuit shown in FIG. 10.

The graph shown in FIG. 8 plots the Resistance of the substance being measured against the Output Voltage 114 of the Constant Current Sink Circuit 112 and shows the voltage increasing as the resistance decreases. This Output Voltage 114 of FIG. 6, ranges from zero volts, or GND 212, to +5 Volts 220. In order to satisfy the inputs to the Divider Circuit 906 of FIG. 10, this voltage must decrease as the resistance decreases and increase as the resistance increases. The Inverter 900 circuit of FIG. 10 with IC2 1004 as the active component, inverts the Constant Current Sink Circuit 112 Output Voltage 114. The Reference voltage 1006 about which this output voltage is inverted has a value of 2.5 Volts. In FIG. 11A the graph entitled "Measured Resistance versus Inverter Circuit Voltage Out" plots voltage values taken from the Inverter output 902 of FIG. 10, for various resistance values of the substance being measured. The resistance of the substance is measured across the Measurement Contacts 102. The voltage output 902 of the Inverter circuit forms the B input to the Divider Circuit 906. In order to establish a reasonable range for the Voltage Out 908, which is the output of the Divider Circuit 906, the A 904 input to the Divider Circuit 906 has a voltage value of −0.1 Volts. The value of C, or Voltage Out 908, is based upon the formula:

$$-10 * \frac{A}{B} = C$$

In one exemplary embodiment, the core of the Divider Circuit 906 is a Multiplier chip, IC4 1016. IC3 1012 may be an operational amplifier that is configured as an inverting summing amplifier and is used to change the Multiplier function of the circuitry to a Divider function. Both IC4 1016 and IC3 1012 may be powered by the +12 Volt 1018 power supply and the −12 Volt 1020 power supply. As with the +5 Volts 220 power supply, these supplies are filtered, regulated D.C. power sources. The increase in the voltage from +5 Volts to '+' and '−' 12 Volts produces an increase in the range of the Voltage Out 908 and result in a greater range of microsiemens (µS) measurements.

Figure 11B:
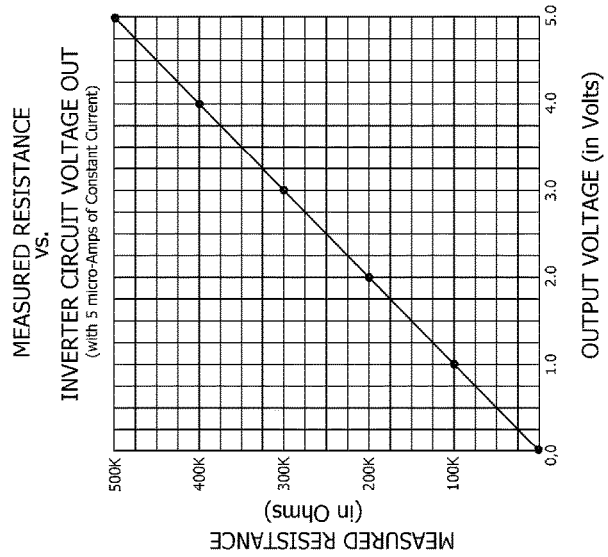
FIG. 11B is a graph showing the resistance of a substance being measured versus the output voltage of the divider circuit shown in FIG. 10.
Figure 12:
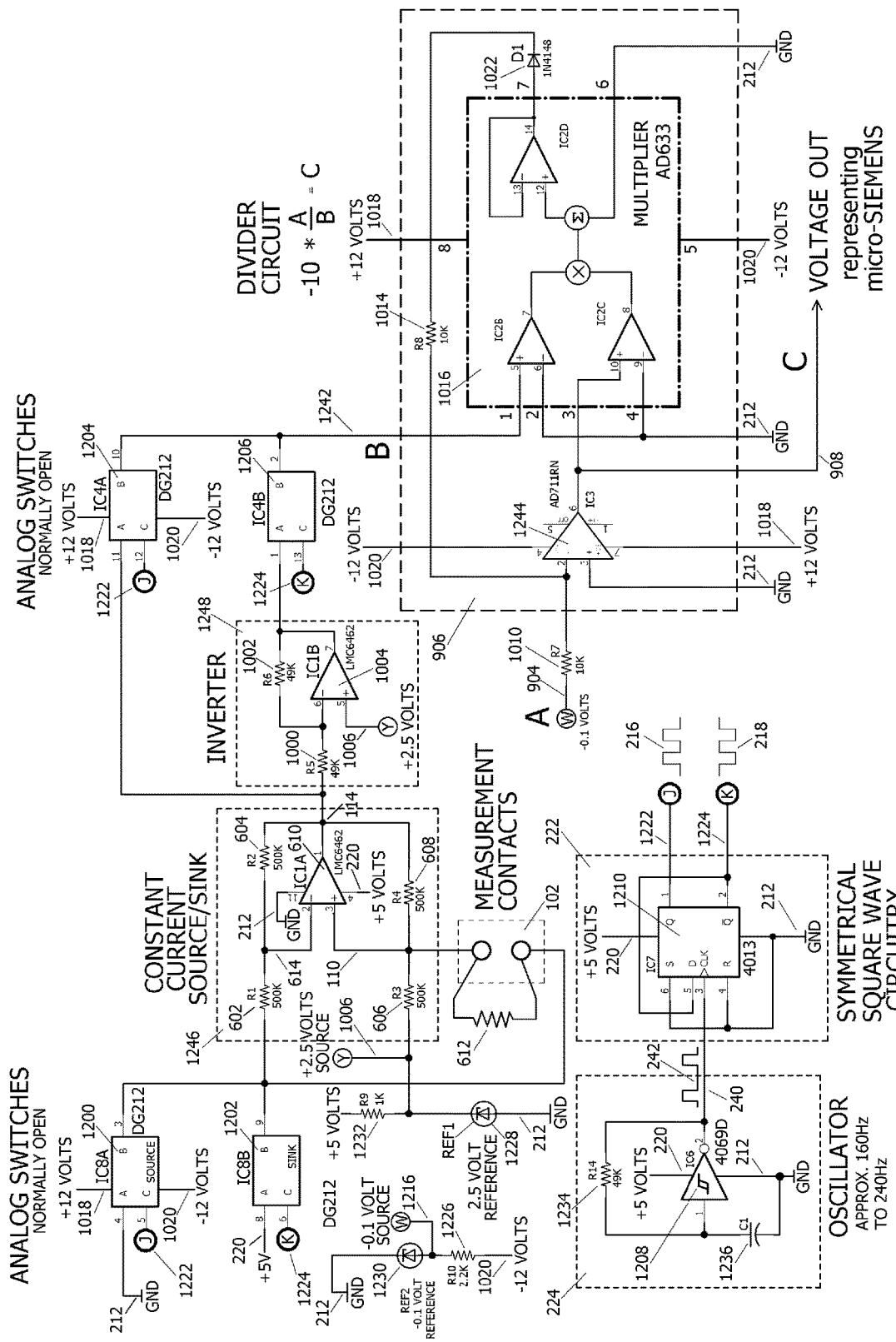
FIG. 12 is a schematic of another exemplary embodiment of a system of conductivity measurement in accordance with the invention.

FIG. 11B shows a graph of Measured Resistance versus Divider Circuit Voltage Out, which plots C, the Voltage Out 908 of FIG. 12 for various values of the resistance of the substances being measured. The Table of Values below the graph in FIG. 11B entitled "Measured Resistance versus Divider Circuit Voltage Out" shows the value of C and a corresponding value of conductivity in microsiemens. Note that the range of microsiemens is equal to the value of C multiplied by 10. There is a direct relationship between microsiemens and the resistance of the substance being measured.

FIG. 12 is of a schematic showing an exemplary embodiment of an apparatus for measuring conductivity without the use of the H-Bridge 100 of FIG. 1. Instead, the Constant Current circuit 112, as shown in FIG. 1, has been re-configured in this embodiment, by means of analog switches 1200, 1202 to both source and sink current. The circuitry of the Measurement Contacts 102 has also been re-configured so that the direction of current flow through the Measurement Contacts 102 can be changed by opening and closing these same analog switches 1200, 1202. The Oscillator and Symmetrical Square Wave Circuitry 108, as shown in FIG. 1, are included in the embodiment shown in FIG. 12 but the Level Shift and Gate Drive circuitry 108 are not included because there are no H-Bridge components that require Gate Drive signals. Instead, in this embodiment, the Symmetrical Square Wave 222 circuitry that is fed by the Oscillator 224 circuitry, will output control signals J 1222 and K 1224 to the four analog switches 1200, 1202, 1204, 1206. The power supplies for the circuitry of FIG. 12 may comprise a regulated +5 Volt 220 power supply, a regulated +12 Volt 1018 power supply and a regulated −12 Volt 1020 power supply. All of these power supplies may be filtered, D.C. (Direct Current) supplies with a common return path at GND (Ground) 212.

In one exemplary embodiment, when the Constant Current circuit 1246 is configured to Source current, the Voltage level of the J 1222 output of the Symmetrical Square Wave Circuitry 222 will be high and the Voltage level of the K 1224 output of the Symmetrical Square Wave Circuitry 222 will be low. This will cause Analog Switch IC8A 1200 to close, while Analog Switch IC8B 1202 will open. This places zero Volts or GND 212 potential at the bottom of the Measurement Probes 102 and zero Volts on the IC8A 1200 end of resistor R1 602. When the Resistance being measured 612 is zero ohms, the '+' input 110 of operational amplifier IC1A 610 is forced to zero Volts or GND 212 potential. Remembering that the two inputs of an operational amplifier are always trying to be at the same potential, the '−' input 614 of operational amplifier IC1A 610 is assumed to be at zero Volts or GND potential. There will be zero Volts on both ends of R1 602 and there must also be zero Volts on both ends of R2 604. This means that the output voltage 114 of IC1A 610 must be zero Volts. The only path for current through the Measurement Probes 102 is through R3 606. R3 606 has the 2.5 Volt Source 1006 on one end and zero Volts on the other. Therefore the current through R3 606 as well as through the Measurement Probes 102 will be 2.5 Volts divide by 500 kOhms or 5 microamps. This is the constant value of current that the Constant Current Source/Sink 1246 circuit will produce in both the Current Sourcing and Current Sinking configurations.

For example, this same Current Sourcing configuration assumes a measurement resistance 612 of 500,000 ohms. The top-most probe of the Measurement Probes 102, and therefore the '+' input 110 of IC1A 610, must be at a potential of 2.5 Volts in order to maintain 5 microamps (µA) of current through the Resistance being measured 612. The '−' input 614 of IC1A 610 is assumed to be at this same potential. Considering that the '−' input 614 is at a 2.5 Volt potential, resistor R1 602 will have 2.5 Volts across it and 5 microamps through it. R1 602 and R2 604 being in series means that 5 microamps must also flow through R2 604. With 2.5 Volts at the junction of R1 602 and R2 604, the output voltage 114 of IC1A 610 must be at a potential of 5 Volts in order to produce 5 µA of current through R2 604. This places 2.5 Volts across R4 608. The current through R4 608 will be 2.5 Volts divided by 500 Kohms or 5 microamps. R3 606 will have 2.5 Volts on each end and will have no current passing through it. R3 606 will contribute all of the current that passes through the measurement resistor 612 that is across the measurement contacts 102. For the Current Sourcing configuration of the Constant Current Source/Sink 1246 circuit the range of the output voltage 114 of IC1A 610 will be from 0 Volts for a 0 ohm Measurement Resistance 612, to 5 Volts for a 500,000 ohm Measurement Resistance 612.

In FIG. 11A, the range of the graph entitled "Measured Resistance versus Inverter Circuit Voltage Out" is from 0 Volts, at 0 ohms to 5 Volts, at 500,000 ohms. This is the same range that has been calculated for the current sourcing configuration described above. Therefore, no signal inversion by the Inverter 1248 circuit of FIG. 12 is necessary when the Constant Current Source/Sink 1246 circuit is configured as a current Source. In this configuration, the Voltage output 114 of IC1A 610, of the Constant Current Source/Sink 1246 circuitry will pass directly to input B 1242 of the Divider Circuit 906 through the Analog Switch, IC4A 1204.

In one embodiment, when the Constant Current Source/Sink 1246 circuit is configured to Sink current, the Voltage level of the J 1222 output of the Symmetrical Square Wave Circuitry 1214 will be low and the Voltage level of the K 1224 output will be high. This will cause Analog Switch IC8A 1200 to be open, while Analog Switch IC8B 1202 will be closed. This places +5 Volts 220 at the bottom of the Measurement Probes 102 and +5 Volts 220 on the IC8B 1202 end of resistor R1 602 of the Constant Current Source/Sink circuit 1246. This is the same configuration that is covered in the explanation of FIG. 6, paragraphs [044] through [054]. The resulting graph associated with the current sinking configuration is found in FIG. 8 and is entitled "Measured Resistance versus Constant Current Circuit Output Voltage." This graph ranges from 0 Volts, at 500 kΩ to 5 Volts, at 0 ohms. In order to achieve the proper Voltage out of the Divider Circuit 906 this range must be converted so as to range from 0 Volts, at 0 ohms to 5 Volts, at 500,000 ohms. This conversion takes place in the Inverter 1248 circuitry and is presented to the B 1242 input of the Divider Circuit 906 through Analog Switch IC4B 1206.

The circuit explanation associated with FIG. 10 includes the operation of the Divider Circuit 906 and is found in paragraph [060]. The Table of Values associated with the graph of FIG. 11B entitled "Measured Resistance Versus Divider Circuit Voltage Out," shows the relationship between measured resistance and microsiemens of conductivity for the circuits of both FIG. 10 and FIG. 12.

Making measurements with a device that has been constructed using the circuitry of FIG. 10 or FIG. 12 involves the following procedure:

a) For substances that are fluid or gas in nature, immerse the MEASUREMENT CONTACTS 102 in the substance to be measured. For substances that are solid in nature, place the MEASUREMENT CONTACTS 102 so that they are in intimate contact with the solid to be measured.

b) Apply filtered direct current (D.C.) power to the device using +12 VOLTS 1018, −12 VOLTS 1020, +2.5 VOLTS 1006 and +5 VOLTS 220 D.C. Power Supplies.

c) Measure and observe the VOLTAGE OUT (C) 908. This Voltage value will represent microsiemens of conductivity as per the Graph and Table of Values of FIG. 11B.

End Procedure

Figure 13:
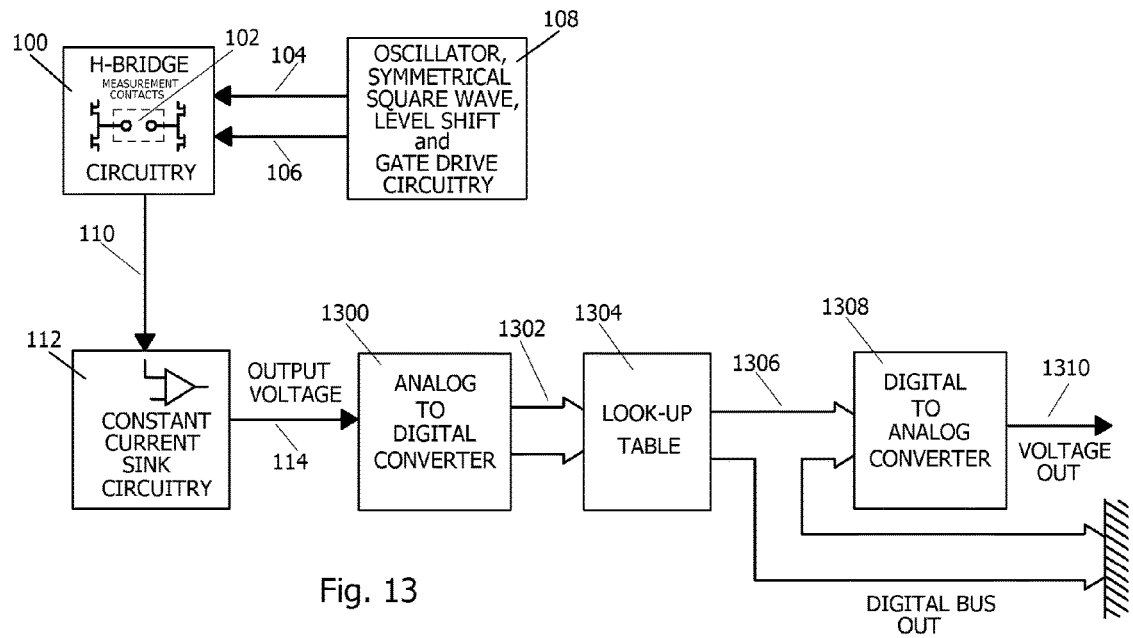
FIG. 13 is a block diagram of a system of conductivity measurement, in accordance with one exemplary embodiment of the invention, that uses digital components to convert the analog signal that represents the resistance of a substance being measured into a digital value of conductance.

FIG. 13 is a block diagram showing an alternate circuit for converting the analog Output Voltage 114 signal at the output of the Constant Current Sink Circuitry 112 into a digital signal 1302. The major components of the apparatus and method, namely the Oscillator, Symmetrical Square Wave, Level Shift and Gate Drive Circuitry 108, the H-Bridge Circuitry 100, and the Constant Current Sink Circuitry 112 remain unchanged.

As previously determined in the explanation of the Constant Current Circuitry 112 of FIG. 6, the Output Voltage 114 is directly related to the resistance of the Substance Being Measured 612 that is across the Measurement Contacts 102. This Output Voltage is sent through an Analog to Digital Converter 1300 that outputs a digital representation of the Output Voltage. As with the Output Voltage 114 signal, this digital signal 1302 represents the resistance of the substance being measured. This digital signal 1302 can then be converted, by means of a Look-Up Table 1304, to a digital signal 1306 that is representative of the conductivity of the substance being measured and that is measured in microsiemens (µS).

In the embodiment shown in FIG. 13, the Output Voltage 114 from the Constant Current Sink Circuitry 112 becomes the input to an Analog-to-Digital Converter 1300. The output of the Analog-to-Digital Converter 1300 is shown in FIG. 13 as a digital bus 1302. This bus 1302 can be either a serial bus or a parallel bus. This bus 1302 contains the Output Voltage 114 value that has been converted to a digital value in the Analog to Digital Converter 1300. The digital bus 1302 may be connected to the input of the Look-Up Table 1304. The Look-up Table matches the converted digital value 1302 with an equivalent digital value representing micro-Siemens of conductivity 1306. This digital conductivity value 1306 can either be directly output as a digital signal, shown as Digital Bus Out 1306, or can be converted, by means of the Digital to Analog Converter 1308 into the Voltage Out 1310 signal that now represents the conductivity of the substance being measured, in units of microsiemens (µS).

Figure 14:
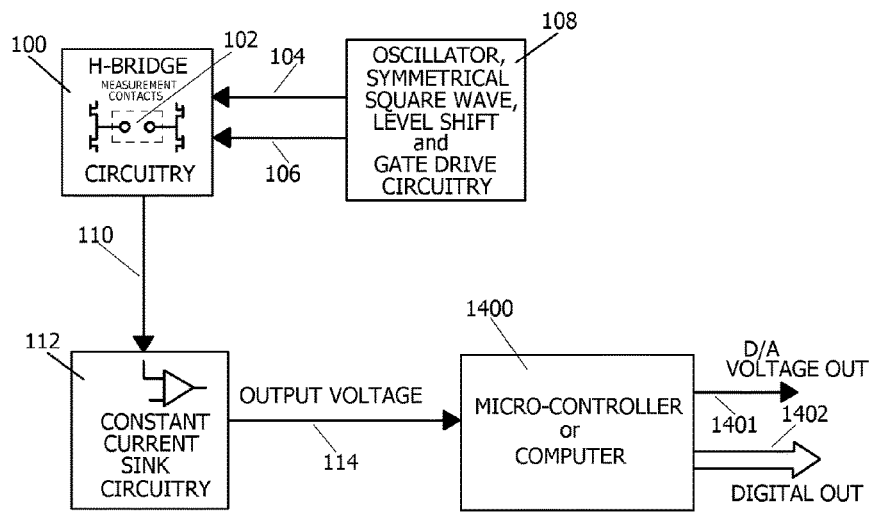
FIG. 14 is a block diagram of a system of conductivity measurement, in accordance with one exemplary embodiment of the invention, that uses a micro-controller or computer to convert the analog signal that represents the resistance of a substance being measured into a digital value of conductance.

FIG. 14 is a block diagram showing another embodiment, an alternate way of converting the voltage that represents the resistance of the substance being measured, across the Measurement Contacts 102, into a digital signal and/or an analog signal that represents the conductivity, in microsiemens, of this substance to be measured. The major components of the method, namely the Oscillator, Symmetrical Square Wave, Level Shift and Gate Drive Circuitry 108, the H-Bridge Circuitry 100, and the Constant Current Sink Circuit 112 remain unchanged.

In this embodiment, the Output Voltage 114 from the Constant Current Sink Circuitry 112 becomes the input to a micro-Controller 1400 or computer. The micro-Controller 1400 can perform the Analog-to-Digital conversion 1300, as shown in FIG. 13, as well as the Look-Up Table operation 1304 shown in FIG. 13. In one embodiment, the micro-controller 1400 may also perform the function of the Digital-to-Analog Converter 1308 of FIG. 13.

The result of these operations is a digital and/or analog value that represents the conductivity, in microsiemens, of the substance being measured across the Measurement Contacts 102. This digital value can be output from the micro-controller 1400 as digital information 1402, on either a serial or a parallel bus, or can be converted to an analog signal 1401, by means of an analog-to-digital converter contained within the microcontroller 1400 or other suitable computer, and output as a voltage 1401 representing the conductivity of the substance being measured, in units of microsiemens (µS).

This disclosure and the accompanying figures illustrate various non-limiting, exemplary, inventive aspects of the Measurement System. It should be appreciated by those skilled in the art that any figures represent conceptual views of illustrative systems. Similarly, it should be appreciated that any block diagrams, circuit diagrams, flow charts, flow diagrams, and the like represent various processes, which may be substantially represented in a computer readable medium and so executed by a computer or processor, whether or not such computer or processor is explicitly shown.

The order in which the various methods and components described in this disclosure is not intended to be construed as a limitation, and any number of the described method steps or system components can be combined in any order to implement the methods and systems, or an alternative methods and systems. Additionally, individual steps or components may be deleted from or added to the methods and systems described in this disclosure without departing from the scope of the subject matter. Furthermore, the methods and systems can be implemented in any suitable hardware, software, firmware, or combination thereof.

The invention claimed is:

1. A circuit for measuring an electrical conductance of a substance, comprising:
   a first electrode and a second electrode;
   an H-bridge circuit driven by oscillating inputs and having a left and a right branch wherein each branch includes two transistors connected in series forming a left node and a right node wherein the left node is connected to the first electrode and the right node is connected to the second electrode, and wherein output of the left branch is electrically connected to the output of the right branch to provide an H-Bridge output signal; and
   a constant current circuit for providing a constant current to the H-bridge wherein the constant current circuit receives the H-bridge output signal and outputs a signal representative of the inverse of a resistance of the substance when the substance is connected across the first and the second electrodes.

2. The circuit for measuring an electrical conductance of a substance in claim 1, further comprising an inverter receiving the output signal from the constant current circuit and outputting a voltage corresponding to the conductance of the substance.

3. The circuit for measuring an electrical conductance of a substance in claim 2, further including a divider circuit to receive and to convert the output voltage from the inverter into a voltage representing the conductance of the substance in microsiemens.

4. The circuit for measuring an electrical conductance of a substance in claim 1, further comprising an analog to digital converter to convert the constant current output into a digital value and a lookup table to convert the digital value into a digital value indicating the conductance of the substance.

5. A method of measuring the electrical conductance of a substance using the circuit recited in claim 1, comprising:
placing the substance in contact with the first and second electrodes;
driving the H-bridge circuit with oscillating inputs to generate an H-bridge output signal;
inputting the H-bridge output signal into the constant current sink circuit; and
outputting a voltage indicative of the inverse resistance of the substance.

6. The method of measuring the electrical conductance of a substance as recited in claim 5, further comprising:
inputting the voltage indicative of the inverse resistance of the substance into an inverter and outputting a voltage indicating the conductance of the substance.

7. The method of measuring the electrical conductance of a substance as recited in claim 6, further comprising:
inputting the voltage from the inverter into a divider circuit and outputting a voltage corresponding to the conductance of the substance in microsiemens.

8. The method of measuring the electrical conductance of a substance as recited in claim 5, further comprising the steps of converting the output voltage into a digital value by an analog-to-digital converter and converting the digital value into a digital value indicative of the conductance of the substance by a lookup table.

* * * * *